US011278485B2

(12) United States Patent
Ishikawa et al.

(10) Patent No.: US 11,278,485 B2
(45) Date of Patent: Mar. 22, 2022

(54) MOISTURIZING TOPICAL PREPARATION

(71) Applicant: OJI HOLDINGS CORPORATION, Tokyo (JP)

(72) Inventors: Kotaro Ishikawa, Tokyo (JP); Takuro Kashiwamura, Tokyo (JP); Takuya Kato, Tokyo (JP); Toru Koga, Tokyo (JP); Suguru Ishikawa, Tokyo (JP)

(73) Assignee: OJI HOLDINGS CORPORATION, Tokyo (JP)

( * ) Notice: Subject to any disclaimer, the term of this patent is extended or adjusted under 35 U.S.C. 154(b) by 0 days.

(21) Appl. No.: 16/617,783

(22) PCT Filed: May 30, 2018

(86) PCT No.: PCT/JP2018/020644
§ 371 (c)(1),
(2) Date: Nov. 27, 2019

(87) PCT Pub. No.: WO2018/221547
PCT Pub. Date: Dec. 6, 2018

(65) Prior Publication Data
US 2020/0146963 A1 May 14, 2020

(30) Foreign Application Priority Data

May 31, 2017 (JP) .............................. JP2017-108001
Sep. 12, 2017 (JP) .............................. JP2017-175133
Dec. 20, 2017 (JP) .............................. JP2017-244051

(51) Int. Cl.
*A61K 8/73* (2006.01)
*A61Q 19/00* (2006.01)

(52) U.S. Cl.
CPC .............. *A61K 8/73* (2013.01); *A61Q 19/007* (2013.01)

(58) Field of Classification Search
CPC ......... A61K 8/73; A61K 31/737; A61P 17/16; A61Q 19/007
USPC ......................................................... 514/54
See application file for complete search history.

(56) References Cited

U.S. PATENT DOCUMENTS

| 4,168,742 | A | 9/1979 | Kluppel et al. |
| 4,699,900 | A | 10/1987 | Bayol et al. |
| 4,713,373 | A | 12/1987 | Bayol et al. |
| 4,727,063 | A | 2/1988 | Naggi et al. |
| 5,516,765 | A | 5/1996 | Andermann |
| 7,902,158 | B2 | 3/2011 | Kuszmann et al. |
| 8,987,216 | B2 | 3/2015 | Kuszmann et al. |
| 8,993,536 | B2 | 3/2015 | Kakehi et al. |
| 2001/0005720 | A1 | 6/2001 | Striker et al. |
| 2003/0109491 | A1 | 6/2003 | Ulmer et al. |
| 2006/0194759 | A1 | 8/2006 | Eidelson |
| 2007/0281893 | A1 | 12/2007 | Kuszmann et al. |
| 2008/0249298 | A1* | 10/2008 | Ulmer ..................... A61P 43/00 536/121 |
| 2010/0055060 | A1 | 3/2010 | Yoshida et al. |
| 2010/0261807 | A1 | 10/2010 | Laine et al. |
| 2011/0118198 | A1 | 5/2011 | Kuszmann et al. |
| 2011/0251154 | A1* | 10/2011 | Stajic ..................... A61P 19/02 514/54 |
| 2011/0281819 | A1 | 11/2011 | Kakehi et al. |
| 2011/0306567 | A1 | 12/2011 | Schofield et al. |

FOREIGN PATENT DOCUMENTS

| CA | 2018133 | A1 | 12/1990 |
| CN | 1051564 | A | 5/1991 |
| CN | 1832966 | A | 9/2006 |
| CN | 101014607 | A | 8/2007 |
| CN | 102061323 | A | 5/2011 |
| CN | 102300870 | A | 12/2011 |
| CN | 102766225 | A | 11/2012 |
| CN | 103320548 | A | 9/2013 |
| CN | 105907896 | A | 8/2016 |
| CN | 106832020 | A | 6/2017 |
| EP | 0 116 801 | B1 | 4/1987 |
| EP | 0889055 | A1 | 7/1999 |
| JP | S48-043100 | B1 | 12/1973 |
| JP | S60-063203 | A | 4/1985 |
| JP | S61-130301 | A | 6/1986 |
| JP | S61-130302 | A | 6/1986 |
| JP | S61-197601 | A | 9/1986 |
| JP | S62-004362 | B2 | 1/1987 |
| JP | H03-20225 | A | 1/1991 |
| JP | H09-509650 | A | 9/1997 |
| JP | H10-195107 | A | 7/1998 |
| JP | 11-180821 | * | 2/1999 | ............... A61K 7/00 |

(Continued)

OTHER PUBLICATIONS

Office Action dated Nov. 16, 2020 in Australian Application No. 2018276567.
"Technology of Wood Chemicals", CMC Publishing Co., Ltd., 2007, p. 108.
Koshijima, "Recent Problems of Hemicellulose Chemistry", Material, 1967, vol. 16, pp. 758-764.
International Preliminary Report on Patentability for PCT/JP2018/007138 dated Oct. 24, 2018 corresponding to U.S. Appl. No. 16/489,074.
International Search Report for PCT/JP2018/007138 dated Mar. 27, 2018 corresponding to U.S. Appl. No. 16/489,074.
Ishihara et al., "Isolation of Xylan from Hardwood by Alkali Extraction and Steam Treatment", Mokuzai Gakkaishi, Journal of Wood Science 1996, vol. 42, No. 12, pp. 1211-1220 (11 pages total).
Kabel et al., "Hydrothermally treated xylan rich by-products yield different classes of xylo-oligosaccharides" Carbohydrate Polymers, 2002, vol. 50, No. 1, pp. 47-56.

(Continued)

Primary Examiner — Ganapathy Krishnan
(74) Attorney, Agent, or Firm — Sughrue Mion, PLLC

(57) ABSTRACT

The present invention provides a novel topical moisturizing preparation containing as an active ingredient at least one selected from pentosan polysulfate; pharmaceutically acceptable salts of pentosan polysulfate; and pharmaceutically acceptable solvates thereof. The topical moisturizing preparation of the present invention, which contains a substance free of animal-derived components as an active ingredient, can be produced as a topical moisturizing preparation free of animal-derived components, as needed.

11 Claims, 1 Drawing Sheet

(56) References Cited

FOREIGN PATENT DOCUMENTS

| | | |
|---|---|---|
| JP | H11-49802 A | 2/1999 |
| JP | H11-180821 A | 7/1999 |
| JP | 2003-183303 A | 7/2003 |
| JP | 2003-221307 A | 8/2003 |
| JP | 2003-221339 A | 8/2003 |
| JP | 2004-513185 A | 4/2004 |
| JP | 2005-501931 A | 1/2005 |
| JP | 2009-196915 A | 9/2009 |
| JP | 2009-532467 A | 9/2009 |
| JP | 2013-177433 A | 9/2013 |
| JP | 2014-129383 A | 7/2014 |
| JP | 2015-038061 A | 2/2015 |
| JP | 2016-514090 A | 5/2016 |
| JP | 6225321 B1 | 11/2017 |
| JP | 6281659 B1 | 2/2018 |
| WO | 1991/016058 A1 | 10/1991 |
| WO | 1995/014491 A3 | 6/1995 |
| WO | 1995/014492 A2 | 6/1995 |
| WO | 1995/014492 A3 | 6/1995 |
| WO | 1998/006409 A2 | 2/1998 |
| WO | 02/041901 A1 | 5/2002 |
| WO | 2005/014656 A1 | 2/2005 |
| WO | 2005/117912 A1 | 12/2005 |
| WO | 2007/014155 A2 | 2/2007 |
| WO | 2007/123800 A2 | 11/2007 |
| WO | 2007/138263 A1 | 12/2007 |
| WO | 2008/107906 A1 | 9/2008 |
| WO | 2009/087581 A1 | 7/2009 |
| WO | 2010/000013 A1 | 1/2010 |
| WO | 2010/089617 A2 | 8/2010 |
| WO | 2010/089617 A3 | 8/2010 |
| WO | 2012/101544 A1 | 8/2012 |
| WO | 2012/114349 A1 | 8/2012 |
| WO | 2013/186857 A1 | 12/2013 |
| WO | 2014/114723 A1 | 7/2014 |
| WO | WO 2014/114723 A1 * 7/2014 ............. C08B 37/00 |
| WO | 2014/122251 A2 | 8/2014 |
| WO | 2014/122251 A3 | 8/2014 |
| WO | 2016/184887 A1 | 11/2016 |
| WO | 2016/191698 A1 | 12/2016 |
| WO | 2018/043667 A1 | 3/2018 |
| WO | 2018/043668 A1 | 3/2018 |

OTHER PUBLICATIONS

Kabel et al., "Complex xylo-oligosaccharides identified from hydrothermally treated Eucalyptus wood and brewery's spent grain", Carbohydrate Polymers, 2002, vol. 50, No. 2, pp. 191-200.

Koutaniemi et al., "Distinct roles of carbohydrate esterase family CE16 acetyl esterases and polymer-acting acetyl xylan esterases in xylan deacetylation" Journal of Biotechnology, 2013, vol. 168, No. 4, pp. 684-692.

Pawar et al., "Acetylation of woody lignocellulose: significance and regulation" Frontiers in Plant Science, 2013, vol. 4, No. 118, pp. 1-8.

International Search Report for PCT/JP2017/031434 dated Oct. 31, 2017 corresponding to U.S. Appl. No. 16/643,265.

Office Action issued by Japanese Patent Office dated Apr. 18, 2017 in application No. 2017-040067.

Office Action issued by Japanese Patent Office dated Oct. 3, 2017 in application No. 2017-166559.

Moure et al., "Advances in the manufacture, purification and applications of xylo-oligosaccharides as food additives and nutraceuticals", Process Biochemistry, 2006, vol. 41, Issue 9, pp. 1913-1923.

Gullón et al., "Structural features and properties of soluble products derived from Eucalyptus globulus hemicelluloses" Food Chemistry, 2011, vol. 127, No. 4, p. 1798-1807.

Gullón et al., "Membrane processing of liquors from Eucalyptus globulus autohydrolysis" Journal of Food Engineering, 2008, vol. 87, No. 2, pp. 257-265.

Ishikawa et al., "Research and development of sulphated hemicellulose (PPS)", The 62nd Japan Technical Association of the Pulp and Paper Industry Annual Meeting, 2019, pp. 1-5.

Scully et al., "The antiheparin effect of a heparinoid, pentosane polysulphate" Biochem. J, 1984, vol. 218, pp. 657-665.

McCarty et al., "Sulfated glycosaminoglycans and glucosamine may synergize in promoting synovial hyaluronic acip synthesie" Medical Hypotheses, 2000, vol. 54, No. 5, pp. 798-802.

Ferrao et al., "The effect of heparin on cell proliferation and type-l collagen synthesis by adult human dermal fibroblasts" Biochimica et Biophysica Acta, 1993, vol. 1180, pp. 225-230.

International Search Report for PCT/JP2018/020644 dated Sep. 4, 2018 corresponding to the present application.

International Search Report for PCT/JP2017/031433 dated Oct. 31, 2017 corresponding to U.S. Appl. No. 16/643,215.

Office Action issued by Japanese Patent Office dated Jan. 8, 2019 in application No. 2018-553269.

Office Action issued by Japanese Patent Office dated Feb. 5, 2019 in application No. 2018-229611.

Hirst et al., "Water-soluble Polysaccharides of Cladophora" Journal of the Chemical Society, 1965, pp. 2958-2967.

International Search Report for PCT/JP2018/033535 dated Nov. 27, 2018.

International Search Report for PCT/JP2018/046537 dated Mar. 5, 2019.

International Search Report for PCT/JP2017/031432 dated Oct. 31, 2017.

Office Action issued by Japanese Patent Office dated Jul. 17, 2019 in application JP2018-516078.

Office Action issued by Japanese Patent Office dated Jul. 17, 2019 in application JP2018-516079.

González et al., "Demonstration of Inhibitory Effect of Oral Shark Cartilage on Basic Fibroblast Growth Factor-Induced Angiogenesis in the Rabbit Cornea" Biol. Pharm. Bull, 2001, vol. 24, No. 2, pp. 151-154.

Swain et al., "Heparin-Binding Growth Factor Blockade with Pentosan Polysulfate" Annals of the New York Academy of Sciences, 1993, vol. 698, pp. 63-70.

Zugmaier et al., "Polysulfated Heparinoids Selectively Inactivate Heparin-Binding Angiogenesis Factors" Annals of the New York Academy of Sciences, 1999, vol. 886, pp. 243-248.

Zugmaier et al., "Inhibition by Pentosan Polysulfate (PPS) of Heparin-Binding Growth Factors Released From Tumor Cells and Blockage by PPS of Tumor Growth in Animals" Journal of the National Cancer Institute, 1992, vol. 84, No. 22, pp. 1716-1724.

Garrote et al., "Non-isothermal autohydroiysis of Eucalyptus wood", Wood Science and Technology, 2002, vol. 36, pp. 111-123.

Sivová et al., "Fagus sylvatica glucuronoxylan sulfate-chemical profile and pharmacological view" Starch, 2015, vol. 68, pp. 621-628.

Rhee et al., "Engineering the Xylan Utilization System in Bacillus subtilis for Production of Acidic Xylooligosaccharides" Applied and Environmental Microbiology, 2014, vol. 80, No. 3, pp. 917-927.

Maekawa et al., "Infrared Spectra of Wood Cellulose and Related Polysaccharide" Kyoto University, Research Institute Report, 1968, vol. 43, pp. 1-8, Summary; cited in Office Action dated Jul. 17, 2018 in JP app No. 2018-516079 and Office Action dated Jul. 17, 2018 in JP app No. 2018-516078.

Kabel et al., "In Vitro Fermentability of Differently Substituted Xylo-oligosaccharides" Journal of Agricultural and Food Chemistry, 2002, vol. 50, pp. 6205-6210.

Office Action issued by Japanese Patent Office dated Oct. 9, 2018 in application JP2018-516078.

International Preliminary Report on Patentability dated Dec. 3, 2019 from the International Bureau in International Application No. PCT/JP2018/020644 corresponding to the present application.

U.S. Appl. No. 16/489,074, filed Aug. 27, 2019 (Kotaro Ishikawa et al).

U.S. Appl. No. 16/643,215, filed Feb. 28, 2020 (Kotaro Ishikawa et al).

U.S. Appl. No. 16/643,265, filed Feb. 28, 2020 (Kotaro Ishikawa et al).

Office Action dated Apr. 27, 2021 in U.S. Appl. No. 16/646,243.

(56) References Cited

OTHER PUBLICATIONS

Office Action dated Mar. 2, 2021 in U.S. Appl. No. 16/489,074.
Stephan Daus et al., "Homogeneous Sulfation of Xylan from Different Sources", Macromolecular Materials and Engineering, 2011, vol. 296, pp. 551-561 (11 pages).
ELMIRON®—100 MG (Pentosan Polysulfate Sodium)Capsules, 2002, https://www.accessdata.fda.gov/drugsatfda_docs/label/2020/020193s014lbl.pdf (14 pages).
Office Action dated Mar. 25, 2021 issued by the Indian Patent Office in Indian Application No. 201947036653.
Takayuki Ohbuchi et al., "Structural Analysis of Neutral and Acidic Xylooligosaccharides from Hardwood Kraft Pulp, and Their Utilization by Intestinal Bacteria in Vitro", Bioscience, Biotechnology, and Biochemistry, vol. 73, No. 9, 2009, pp. 2070-2076 (8 pages total).
Office Action dated Jun. 2, 2021, from the United States Patent and Trademark Office in U.S. Appl. No. 16/643,215.
Stephen Dealler et al., "Pentosan polysulfate as a prophylactic and therapeutic agent against prion disease", IDrugs, vol. 6, No. 5, Jun. 1, 2003, pp. 470-478, XP055777416 (10 pages total).
Extended European Search Report dated Feb. 26, 2021 from the European Patent Office in Application No. 16/643,265, corresponding to U.S. Appl. No. 16/643,265.
Extended European Search Report dated Feb. 3, 2021, from the European Patent Office in EP application No. 18809395.9.
Teleman et al., "Characterization of O-acetyl-(4-O-methylglucurono)xylan isolated from birch and beech", Carbohydrate Research, 2002, vol. 337, pp. 373-377 (5 pages total).
Office Action dated Sep. 17, 2021 by Indian Patent Office in Indian Application No. 202047012044.
Office Action dated Aug. 30, 2021 by China National Intellectual Property Administration in Chinese Application No. 201780094371.2.
Mi et al., "Preparation of corn stover pentosan sulfate", Journal of Changchun University of Technology (Natural Science Edition), 2014, vol. 35, No. 6, pp. 716-719 (4 page total).
Extended European Search Report dated Sep. 29, 2021 by European Patent Office in European Application No. 18890627.5.
Herbert et al., "Activity of Pentosan Polysulphate and Derived Compounds on Vascular Endothelial Cell Proliferation and Migration Induced by Acidic and Basic FGF In Vitro", Biochemical Pharmacology, 1988, vol. 37, No. 22, pp. 4281-4288 (8 pages total).
Office Action dated Oct. 26, 2021 in U.S. Appl. No. 16/955,641.
Gura, "Cancer Models: Systems for Identifying New Drugs Are Often Faulty", Science, 1997, vol. 278, No. 5340, pp. 1041-1042 (6 pages total).
"The Merck Manual", Sixteenth Edition, 1992, pp. 339-342 and 1488-1490 (6 pages total).
Smith et al., "Cancer, inflammation and the AT1 and AT2 receptors", Journal of Inflammation, 2004, vol. 1, No. 3, pp. 1-12 (12 pages total).
Vergnolle et al., "Protease-activated receptors and inflammatory hyperalgesia", Mem Inst Oswaldo Cruz, Rio de Janeiro, 2005, vol. 100 (Suppl. I), pp. 173-176 (4 pages total).
Douglass et al., "1. Diagnosis, treatment and prevention of allergic disease: the basics", MJA Practice Essentials—Allergy, 2006, vol. 185, No. 4, pp. 228-233 (6 pages total).
Office Action dated Oct. 25, 2021 issued by China National Intellectual Property Administration in Chinese Patent Application No. 201880058953.X, which corresponds to U.S. Appl. No. 16/646,243.
Communication dated Jan. 4, 2022 from the Indian Patent Office in Indian Application No. 202047029636, corresponding to U.S. Appl. No. 16/955,641.

* cited by examiner

MOISTURIZING TOPICAL PREPARATION

CROSS REFERENCE TO RELATED APPLICATIONS

This application is a National Stage of International Application No. PCT/JP2018/020644 filed May 30, 2018, claiming priority based on Japanese Patent Application No. 2017-108001 filed May 31, 2017, Japanese Patent Application No. 2017-175133 filed Sep. 12, 2017, and Japanese Patent Application No. 2017-244051 filed Dec. 20, 2017.

The present invention relates to a topical moisturizing preparation.

BACKGROUND ART

Conventionally, glycerin, propylene glycol, sorbitol, diethylene glycol monoethyl ether, and the like are known as moisturizers. Further, polysulfated mucopolysaccharides, such as chondroitin sulfate, are also used as moisturizers (for example, Patent Literature (PTL) 1). Polysulfated mucopolysaccharides, such as chondroitin sulfate, are known as heparinoid substances (heparins), and are extracted from the organs of animals, such as bovines and pigs.

Pentosan polysulfate is known as an alternative heparin substance that can be used as a therapeutic agent for thrombosis, osteoarthritis, etc. (for example, Patent Literature (PTL) 2). Pentosan polysulfate can be obtained by sulfating a plant-derived xylooligosaccharide.

CITATION LIST

Patent Literature

PTL 1: JPS62-4362A
PTL 2: WO2010/000013

SUMMARY OF INVENTION

Technical Problem

An object of the present invention is to provide a novel topical moisturizing preparation.

Solution to Problem

Pentosan polysulfate is known as an alternative heparin substance that can be used as a therapeutic agent for thrombosis, osteoarthritis and the like. Since heparin is a substance derived from specific animals, there are cases where its use as a moisturizer causes hesitation from the viewpoint of religious ethics etc. Pentosan polysulfate can be produced from a plant-derived raw material; however, the moisturizing action of pentosan polysulfate was unknown. Accordingly, the present inventors conducted extensive research. As a result, the inventors have found that pentosan polysulfate can exhibit excellent efficacy as a topical moisturizing preparation.

Specifically, the present invention provides the following [1] to [7].

[1] A topical moisturizing preparation comprising, as an active ingredient, at least one selected from pentosan polysulfate; pharmaceutically acceptable salts of pentosan polysulfate; and pharmaceutically acceptable solvates thereof.

[2] The topical moisturizing preparation according to [1], wherein the pentosan polysulfate has a uronic acid content of 0.0% by mass to 15.0% by mass.

[3] The topical moisturizing preparation according to [2], wherein the pentosan polysulfate has a uronic acid content of 7.0% by mass to 15.0% by mass, and an acetyl group content of 0% by mass to 2.0% by mass.

[4] The topical moisturizing preparation according to [2], wherein the pentosan polysulfate has a uronic acid content of 0.0% by mass to 6.0% by mass.

[5] The topical moisturizing preparation according to any one of [1] to [4], which comprises pentosan polysulfate sodium as a pharmaceutically acceptable salt of pentosan polysulfate.

[6] The topical moisturizing preparation according to any one of claims 1 to 5, wherein the pentosan polysulfate has a dispersion degree of 1.00 or more and 1.40 or less.

[7] The topical moisturizing preparation according to any one of [1] to [6], which is an aqueous solution containing pentosan polysulfate, a pharmaceutically acceptable salt of pentosan polysulfate, and a pharmaceutically acceptable solvate thereof, in an amount of 0.05% by mass or more and 40% by mass or less, based on the total mass of the topical moisturizing preparation.

From another point of view, the present invention further provides:

use of at least one selected from pentosan polysulfate; pharmaceutically acceptable salts of pentosan polysulfate; and pharmaceutically acceptable solvates thereof;

use of at least one compound for the production of a topical moisturizing preparation, the compound being selected from pentosan polysulfate, pharmaceutically acceptable salts of pentosan polysulfate, and pharmaceutically acceptable solvates thereof; and a moisturizing method comprising applying to the skin of a human or an animal at least one selected from pentosan polysulfate; pharmaceutically acceptable salts of pentosan polysulfate; and pharmaceutically acceptable solvates thereof, in an amount that is effective dose for a moisturizing action.

Advantageous Effects of Invention

According to the present invention, a novel topical moisturizing preparation is provided. Since the topical moisturizing preparation of the present invention comprises a substance free of animal-derived components as an active ingredient, the preparation can be produced as a topical moisturizing preparation free of animal-derived components, as needed. Furthermore, quality control of the topical moisturizing preparation of the present invention is relatively easy.

DESCRIPTION OF EMBODIMENTS

Figure 1:
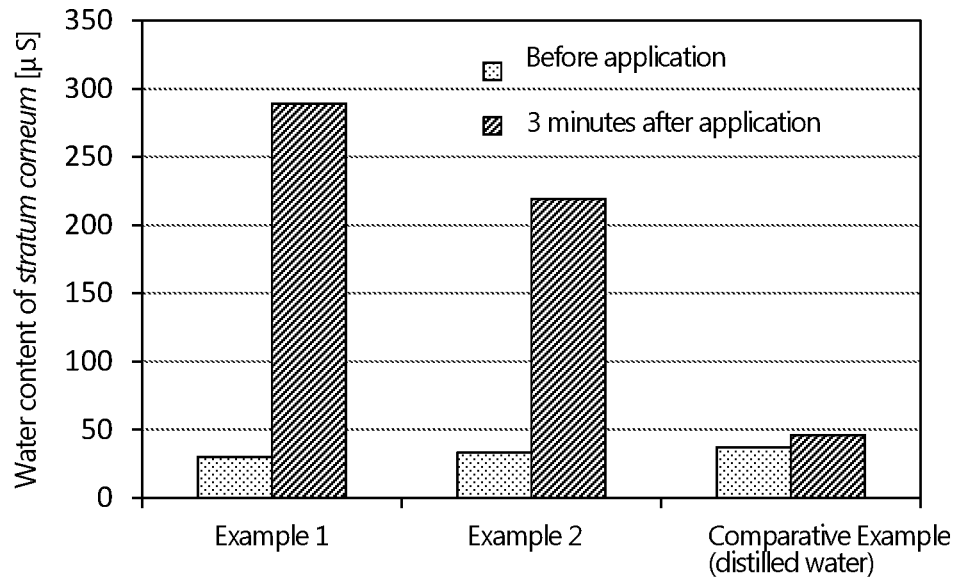
FIG. 1 is a graph showing the water content of stratum corneum before and after application of the topical preparations obtained in the Examples and the Comparative Example.

The present invention is described below in detail. The constituent features may be described below based on typical embodiments and specific examples; however, the present invention is not limited to such embodiments.

Topical Moisturizing Preparation

The topical moisturizing preparation (moisturizer) of the present invention contains at least one selected from pentosan polysulfate; pharmaceutically acceptable salts of pentosan polysulfate; and pharmaceutically acceptable solvates of either pentosan polysulfate or pharmaceutically acceptable salts of pentosan polysulfate. In the present description, pentosan polysulfate, pharmaceutically acceptable salts of pentosan polysulfate, pharmaceutically acceptable solvates of pentosan polysulfate, and pharmaceutically acceptable solvates of pharmaceutically acceptable salts of pentosan polysulfate may be collectively referred to as pentosan polysulfate.

The topical moisturizing preparation of the present invention contains pentosan polysulfate as an active ingredient for moisturizing action. The phrase "containing . . . as an active ingredient" as used herein means containing as a main active ingredient, or means containing in an amount such that the effect is provided. That is, the topical moisturizing preparation of the present invention has at least a moisturizing effect. The topical moisturizing preparation of the present invention can exhibit an excellent moisturizing effect based on pentosan polysulfate contained as an active ingredient for moisturizing action. The topical moisturizing preparation can be used, for example, as a topical preparation for maintaining the water content of stratum corneum on the skin surface, or as a topical preparation for increasing the water content of stratum corneum on the skin surface.

Pentosan polysulfate, which is an active ingredient of the topical moisturizing preparation of the present invention, is known as an active ingredient of medicine, such as therapeutic agents for osteoarthritis (for example, PTL 2). The topical moisturizing preparation of the present invention may have a pharmacological effect other than the moisturizing effect derived from the activity of pentosan polysulfate contained as an active ingredient. Furthermore, the topical moisturizing preparation of the present invention may have a pharmacological effect, other than the moisturizing effect, derived from the activity of a component other than pentosan polysulfate. For example, in addition to the moisturizing effect, the topical moisturizing preparation of the present invention can also exhibit an anti-inflammatory effect, a skin anti-aging effect, a whitening effect, an anti-allergic effect, and the like. When the topical moisturizing preparation of the present invention exhibits an anti-inflammatory effect, for example, the topical moisturizing preparation of the present invention can be used as a topical anti-inflammatory preparation (anti-inflammatory agent) having a moisturizing action.

The topical moisturizing preparation of the present invention can be applied to humans or animals (other than humans). The topical moisturizing preparation of the present invention is preferably applied to the skin or mucous membrane of a human or an animal, more preferably to the skin or mucous membrane of a human, and even more preferably to the skin of a human.

The dosage form of the topical moisturizing preparation is not particularly limited, and may be a liquid, an emulsion, a gel, a spray, a mousse, or the like; the dosage form is preferably a liquid. Specific examples of topical moisturizing preparations include various forms such as ointments, various cosmetic creams, emulsions, lotions, beauty essences, packs, lip balms, lipsticks, under-makeups, foundations, sun creams, body rinses, jelly preparations, and aerosols. The topical moisturizing preparation of the present invention is preferably in the form of a lotion.

When the topical moisturizing preparation of the present invention is to be prepared in the form of a liquid, the topical moisturizing preparation may be formed into, for example, an aqueous solution, which is prepared by dissolving pentosan polysulfate in water. The topical moisturizing preparation in the form of such an aqueous solution preferably contains pentosan polysulfate in an amount of 0.05% by mass or more, more preferably 0.1% by mass or more, and even more preferably 0.3% by mass or more, based on the total mass of the topical moisturizing preparation. On the other hand, the topical moisturizing preparation preferably contains pentosan polysulfate in an amount of 50% by mass or less, more preferably 40% by mass or less, and even more preferably 30% by mass or less, based on the total mass of the topical moisturizing preparation. When the pentosan polysulfate content of the topical moisturizing preparation is within the above-described range, the moisturizing effect is more effectively exhibited.

The topical moisturizing preparation of the present invention may also contain components other than pentosan polysulfate, as desired. Examples of such other components include glycerin, propylene glycol, sorbitol, diethylene glycol monoethyl ether, and polysulfated mucopolysaccharides such as chondroitin sulfate; other moisturizers; anti-inflammatory agents or beauty ingredients known to be added to external preparations or cosmetics; and the like. The topical moisturizing preparation of the present invention may also include, for example, oily bases, surfactants, alcohols, thickeners, gelling agents, antioxidants, preservatives, bactericides, chelating agents, pH adjusters, ultraviolet absorbers, whitening agents, solvents, exfoliating agents, solubilizers, antipruritic agents, antiperspirants, fresheners, reducing agents/oxidizing agents, polymer powders, vitamins and/or derivatives thereof, saccharides and/or derivatives thereof, organic acids, inorganic powders, fragrances, colorings, pigments, and like components known as additives for pharmaceutical or cosmetic products. The topical moisturizing preparation of the present invention preferably does not contain any animal-derived components from the viewpoint of providing a topical moisturizing preparation free of animal-derived components; however, the preparation may contain an animal-derived component according to the purpose.

Pentosan Polysulfate

Pentosan polysulfate has a structure in which at least one hydroxyl group of xylooligosaccharide is sulfated. The pentosan polysulfate is preferably obtained by sulfating acidic xylooligosaccharide or neutral xylooligosaccharide, and more preferably obtained by sulfating acidic xylooligosaccharide. Among xylooligosaccharides having a structure in which xylooligosaccharide is sulfated, neutral xylooligosaccharide is one that does not contain uronic acid. Acidic xylooligosaccharide is one in which at least one uronic acid is bound to at least one xylose unit in one xylooligosaccharide molecule. That is, acidic xylooligosaccharide has at least one uronic acid residue as a side chain in one xylooligosaccharide molecule. The average number of uronic acid residues per molecule of acidic xylooligosaccharide is preferably 1 or more and 3 or less, more preferably 1 or more and 2 or less. The number of uronic acid residues contained in one xylooligosaccharide molecule can be measured by the carbazole-sulfuric acid method, or the colorimetric method using sodium tetraborate. The uronic acid content (mass %) of pentosan polysulfate is a value calculated from the number of uronic acid residues in a predetermined amount of pentosan polysulfate, obtained by the carbazole-sulfuric acid method, as described in Examples.

In the present specification, pentosan polysulfate includes salts of pentosan polysulfate, solvates of pentosan polysulfate, and solvates of salts of pentosan polysulfate. Salts of pentosan polysulfate are preferably pharmaceutically acceptable salts; and examples include pentosan polysulfate sodium, pentosan polysulfate potassium, pentosan polysulfate calcium, and the like. The solvates are preferably pharmaceutically acceptable solvates. Examples of solvates include water.

The pentosan polysulfate preferably has a structure represented by the following formula II.

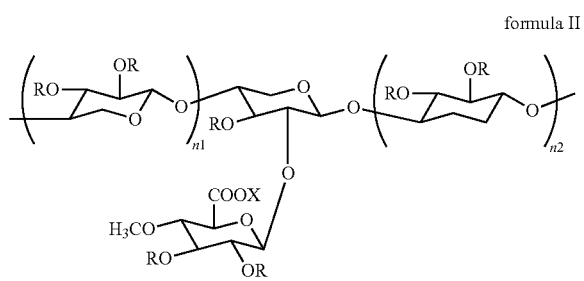

formula II

In formula II, R each independently represents a hydrogen atom, —COCH$_3$, or —SO$_3$X$^1$; and at least one R in the molecule of pentosan polysulfate is —SO$_3$X$^1$. X$^1$ is a hydrogen atom, or a monovalent or divalent metal; and X$^1$ preferably a hydrogen atom, sodium, potassium, or calcium, more preferably sodium, potassium, or calcium, and particularly preferably sodium. X is a hydrogen atom, or a monovalent or divalent metal; and X is preferably a hydrogen atom, sodium, potassium, or calcium, more preferably sodium, potassium, or calcium, and particularly preferably sodium. n1 and n2 each independently represent an integer of 0 or more and 30 or less, and at least one of n1 and n2 is an integer of 1 or more.

In formula II, X is preferably a monovalent or divalent metal, and the compound is preferably a pharmaceutically acceptable salt of pentosan polysulfate. For example, X is preferably sodium, potassium, or calcium. In this case, the pentosan polysulfate salt is pentosan polysulfate sodium, pentosan polysulfate potassium, or pentosan polysulfate calcium. Among these, the salt of pentosan polysulfate is particularly preferably pentosan polysulfate sodium. The topical moisturizing preparation preferably contains pentosan polysulfate sodium as a salt of pentosan polysulfate.

In formula II, n1+n2 is preferably 1 to 90, more preferably 1 to 27, even more preferably 2 to 18, and particularly preferably 3 to 10.

One pentosan polysulfate molecule may contain one structure represented by formula II, or two or more structures represented by formula II. When one pentosan polysulfate molecule contains two or more structures represented by formula II, the pentosan polysulfate preferably contains the structures as structures representing repeating units. The pentosan polysulfate may be a structure represented by formula II, or may have a structure consisting only of structures represented by formula II as repeating units, or may further contain other structural units. The structure represented by formula II or a structure consisting only of structures represented by formula II as repeating units is preferable.

The pentosan polysulfate preferably does not contain an arabinose-derived sugar unit (arabinofuranose residue).

The portion that is an end of the structure represented by formula II and that does not bind to a structure represented by formula II may be —OR. That is, —OR may bind to the left terminus (n1 side) of formula II, whereas —R may bind to the right terminus (n2 side) of formula II. It is particularly preferable that —OR$^X$ binds to the left terminus (n1 side) of formula II, and —R$^X$ binds to the right terminus (n2 side) of formula II. In formula II, R$^X$ is a hydrogen atom or —SO$_3$X$^1$; X$^1$ is a hydrogen atom or a monovalent or divalent metal; and X$^1$ is preferably a hydrogen atom, sodium, potassium, or calcium, more preferably sodium, potassium, or calcium, and particularly preferably sodium.

The pentosan polysulfate may be a mixture of molecules represented by formula II, which are different from each other in the values of n1 and n2, the kind of substituent R, and/or the degree of substitution.

The pentosan polysulfate may contain a certain amount of xylose units to which an acetyl group (—COCH$_3$) as well as uronic acid residue(s) bind. For example, the acetyl group content of pentosan polysulfate may be more than 2.0 mass % and 6.0 mass % or less.

The pentosan polysulfate preferably has an acetyl group content of 0 to 2.0 mass %, preferably 0 to 1.0 mass %, more preferably 0 to 0.4 mass %, and even more preferably 0 to 0.3 mass %. It is particularly preferable that pentosan polysulfate has an acetyl group content of substantially 0 mass %. The number of Rs that represent —COCH$_3$ preferably accounts for 8% or less, more preferably 4% or less, and even more preferably 1% or less, of the total number of Rs in formula II. It is particularly preferable that none of the Rs is —COCH$_3$. That is, it is particularly preferable that each R independently represents a hydrogen atom or —SO$_3$X.

In order to obtain pentosan polysulfate having an acetyl group content of 0 to 2.0 mass %, the pentosan polysulfate is preferably produced through a deacetylation step described later. When pentosan polysulfate has a low acetyl group content, pentosan polysulfate sodium can be produced from acidic xylooligosaccharide with a high yield.

The acetyl group content of polysulfate pentosan can be calculated from the integral ratio of peaks in $^1$H-NMR measurement. Specifically, first, $^1$H-NMR measurement is performed using a $^1$H-NMR measurement solution containing a specific amount of pentosan polysulfate and a specific amount of an internal standard substance. In the obtained spectrum, by comparing the integral ratio of the peak for a specific group of the internal standard substance and the peak for acetyl group, the molar amount of acetyl groups in the solution is obtained. The molar amount of acetyl groups is then multiplied by 43; and the obtained value is divided by the average molecular weight obtained separately, so as to obtain the mass % of acetyl groups.

The weight average molecular weight (Mw) of pentosan polysulfate is not particularly limited, and may be, for example, 4000 or less, 3900 or less, or 3800 or less. In this case, pentosan polysulfate preferably has a weight average molecular weight (Mw) of 1000 or more, more preferably 1500 or more, and even more preferably 2000 or more. The weight average molecular weight (Mw) of pentosan polysulfate may be greater than 4000, may be 5000 or more, may be 8000 or more, may be 10000 or more, may be 15000 or more, and may be 20000 or more. In this case, the weight average molecular weight (Mw) of pentosan polysulfate is preferably 50000 or less, more preferably 45000 or less, and even more preferably 40000 or less. The weight average molecular weight (Mw) of pentosan polysulfate can also be adjusted as appropriate according to the efficacy required of the topical moisturizing preparation.

The number average molecular weight (Mn) of pentosan polysulfate is not particularly limited, and may be, for example, 4000 or less, 3900 or less, 3800 or less, or 3750 or less. In this case, the lower limit of the number average molecular weight (Mn) of pentosan polysulfate is preferably 1000.

The number average molecular weight (Mn) of pentosan polysulfate may be 5000 or more, 7000 or more, 10000 or more, 15000 or more, or 20000 or more.

The weight average molecular weight (Mw) and the number average molecular weight (Mn) of pentosan polysulfate can be measured by GPC (gel permeation chromatography). As the GPC column, TSKgel G2000SWXL, manufactured by Tosoh Corporation, can be used. As GPC conditions, for example, the following conditions are used.

Eluent: 300 mM sodium chloride/50 mM sodium acetate buffer (pH 4.0)
Flow rate: 1 mL/min
Measurement temperature: 40° C.
Detector: refractive index detector
Analysis time: 15 minutes The dispersion degree of pentosan polysulfate is preferably 1.00 or more to 1.40 or less, more preferably 1.00 or more to 1.35 or less. The dispersion degree of pentosan polysulfate may be 1.05 or more, or may be 1.10 or more. The dispersion degree (D) of pentosan polysulfate is calculated by the following formula.

Dispersion degree (D)=Weight average molecular weight (Mw)/Number average molecular weight (Mn)

By setting the dispersion degree of pentosan polysulfate within the above-described range, the topical moisturizing preparation can more effectively exhibit various efficacies, such as moisturizing effect.

In pentosan polysulfate, the number of Rs that represent —$SO_3X$ preferably accounts for 50% or more, more preferably 70% or more, and even more preferably 90% or more of the total number of Rs in formula II.

The above proportion does not have to be met by a single molecule, but may be satisfied by pentosan polysulfate as an entire mixture of individual molecules.

The sulfur content of pentosan polysulfate is preferably 10.0 mass % or more, more preferably 12.0 mass % or more, and even more preferably 15.0 mass % or more. The sulfur content of pentosan polysulfate is preferably 20.0 mass % or less. Here, the sulfur content of pentosan polysulfate is a value determined according to the oxygen flask combustion method described in the Japanese Pharmacopoeia.

The uronic acid content of pentosan polysulfate is preferably 0.0 mass % to 15.0 mass %. The value referred to herein to describe the uronic acid content does not have to be met by a single molecule, but may be satisfied by pentosan polysulfate as an entire mixture of individual molecules.

In an embodiment wherein pentosan polysulfate has a high uronic acid content, pentosan polysulfate preferably has a uronic acid content of 7.0 mass % to 15.0 mass %, more preferably 7.5 mass % to 14.0 mass %, and even more preferably 7.7 mass % to 13.0 mass %. In this embodiment, pentosan polysulfate preferably has an acetyl content of 0 to 2.0 mass %, more preferably 0 to 1.0 mass %, even more preferably 0 to 0.4 mass %, and particularly preferably 0 to 0.3 mass %. It is most preferable that pentosan polysulfate has an acetyl group content of substantially 0 mass %. In this embodiment, pentosan polysulfate preferably has a weight average molecular weight (Mw) of 5000 or less, and more preferably 4000 or less. Further, the number average molecular weight (Mn) is preferably 5000 or less, and more preferably 4000 or less.

As shown in the Examples below, pentosan polysulfate with a high uronic acid content has a high pH buffering action. Therefore, by using pentosan polysulfate with a high uronic acid content as an active ingredient of the topical moisturizing preparation of the present invention, the pH of the topical moisturizing preparation can be easily adjusted, for example, even if no pH adjuster or pH buffer is added, or even if the amount of pH adjuster or pH buffer used is small.

The concentration of pentosan polysulfate in the aqueous solution for fully demonstrating pH buffering action is preferably 10 to 500 mg/mL, and more preferably 50 to 300 mg/mL.

In an embodiment where pentosan polysulfate has a low uronic acid content, pentosan polysulfate preferably has a uronic acid content of 0.0 mass % to 4.0 mass %, more preferably 0.0 mass % to 2.0 mass %, and even more preferably 0.0 mass % to 1.0 mass %. It is particularly preferable that the pentosan polysulfate of the present invention has a uronic acid content of substantially 0.0 mass %.

Specifically, pentosan polysulfate may have a structure represented by formula I.

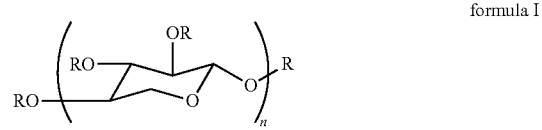

formula I

In formula I, each R independently represents a hydrogen atom, —$COCH_3$, or —$SO_3X$; at least one R in the molecule is —$SO_3X$; X is a hydrogen atom or a monovalent or divalent metal; and n represents an integer of 1 or more and 30 or less.

The compound represented by formula I is preferably a compound represented by the following formula $I^X$. More specifically, the terminal R is preferably not —$COCH_3$.

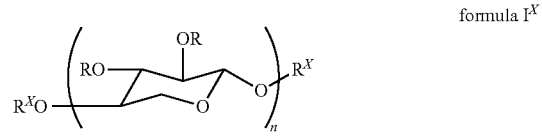

formula $I^X$

In formula $I^X$, each $R^X$ independently represents a hydrogen atom or —$SO_3X$.

As shown in the Examples below, when pentosan polysulfate sodium has a low uronic acid content, a pentosan polysulfate sodium powder can be produced from a xylooligosaccharide powder with a high yield. Furthermore, pentosan polysulfate sodium in the form of an aqueous solution is less likely to turn yellow, even after long-term storage at a high temperature. Accordingly, by using pentosan polysulfate with a low uronic acid content as an active ingredient of the topical moisturizing preparation of the present invention, a topical moisturizing preparation that is less likely to undergo discoloration can be obtained.

Method for Producing Pentosan Polysulfate

Pentosan polysulfate can also be obtained, for example, by a method for producing pentosan polysulfate, comprising a first step of obtaining a xylooligosaccharide (acidic xylooligosaccharide, neutral xylooligosaccharide, or a mixture of these xylooligosaccharides) from a plant-derived raw material; and a second step of obtaining pentosan polysulfate from the xylooligosaccharide. The first step includes a step of depolymerizing a plant-derived raw material. By performing the step of depolymerizing a plant-derived raw material and a sulfation step in this order, pentosan polysulfate can be efficiently produced. This can increase the yield of pentosan polysulfate; and also makes it possible to reduce the production cost of pentosane polysulfate, thus providing pentosan polysulfate less expensively.

Neutral xylooligosaccharide can be produced by polymerizing D-xylose.

The method for producing pentosan polysulfate may further comprise a deacetylation step. By including the deacetylation step, pentosan polysulfate with a low acetyl content can be produced.

The average degree of polymerization of xylooligosaccharide to be subjected to sulfation is preferably adjusted, as appropriate, according to the molecular weight of pentosan polysulfate to be obtained as a final product.

The average degree of polymerization of xylooligosaccharide can be calculated by dividing the total sugar amount of the xylooligosaccharide by the amount of reducing sugar. In calculation of the total sugar amount, first, a xylooligosaccharide solution is maintained at 50° C. and centrifuged at 15000 rpm for 15 minutes. Thereafter, the total sugar amount of a supernatant is quantified by a phenol-sulfuric acid method ("Kangento no Teiryo-Ho (Method of Quantifying Reducing Sugar)"; published by Gakkai Shuppan Center). The calibration curve to be used in the quantification is produced using D-xylose (Wako Pure Chemical Industries, Ltd.). The amount of reducing sugar is quantified by the Somogyi-Nelson method ("Kangento no Teiryo-Ho (Method of Quantifying Reducing Sugar)"; published by Gakkai Shuppan Center). The calibration curve to be used in this quantification is also produced using D-xylose (Wako Pure Chemical Industries, Ltd.).

Plant-Derived Raw Material

In the present invention, a xylooligosaccharide (acidic xylooligosaccharide or neutral xylooligosaccharide, or a mixture of these xylooligosaccharides) can be obtained by depolymerizing a plant-derived raw material. Examples of plant-derived raw materials include wood-derived raw materials, seed-derived raw materials, grain-derived raw materials, fruit-derived raw materials, and the like. Further, examples of plant-derived materials include cottons such as cotton linter and cotton lint; herbaceous plants such as kenaf, hemp, ramie, and rice straw; and the like. As the plant-derived raw material, the above-mentioned raw materials derived from various sources may also be used in combination.

Among these, wood-derived raw materials are preferably used as the plant-derived raw material. Examples of usable wood-derived raw materials include softwoods, hardwoods, or like wood raw materials. The wood-derived raw material is preferably at least one selected from softwoods and hardwoods; and hardwoods are more preferably used. The wood-derived raw material may be a mixture of softwoods and hardwoods. A bark may also be used as the wood-derived raw material.

Examples of hardwoods include beech, Eucalyptus globulus, Eucalyptus grandis, Eucalyptus urograndis, Eucalyptus pellita, Eucalyptus braciana, Acacia mearnsii, and the like. Examples of softwoods include Japanese cedar, Japanese cypress, pine, hiba, Japanese hemlock, and the like.

The wood-derived raw material preferably has a specific gravity of 450 kg/m$^3$ or more and 700 kg/m$^3$ or less, and more preferably 500 kg/m$^3$ or more and 650 kg/m$^3$ or less. By setting the specific gravity of the wood-derived raw material to be within the above-described range, the efficiency of producing xylooligosaccharide can be further enhanced.

The wood-derived raw material is preferably wood chips obtained by crushing one or more of the above-mentioned woods. By using wood chips as a plant-derived raw material, the depolymerization of a plant-derived raw material can be efficiently performed, and the efficiency of producing xylooligosaccharide can be enhanced.

First Step

Depolymerization Step

The method for producing pentosan polysulfate comprises a first step of depolymerizing a plant-derived raw material to obtain a xylooligosaccharide. The step of depolymerizing a plant-derived material is a step of chemically and/or physically decomposing a plant-derived material to produce a xylooligosaccharide. Examples of the chemical and/or physical decomposition step include a heat treatment step, an alkali treatment step, an acid treatment step, an enzyme treatment step, an ionic liquid treatment step, a catalytic treatment step, and the like. Among these steps, the depolymerization step is preferably at least one selected from a heat treatment step, an alkali treatment step, and an enzyme treatment step; and is more preferably a heat treatment step. The heat treatment step may be a heating and pressurizing step. The depolymerization step is preferably performed under non-alkaline conditions (pH 9 or less, preferably pH 8 or less).

The heat treatment step is a step of heating a plant-derived raw material in the presence of a solution. Since the plant-derived raw material is hydrolyzed in such a heat treatment step, the heat treatment step is sometimes referred to as a hydrolysis treatment step or a pre-hydrolysis treatment step. The solution used in the heat treatment step is preferably water. The ratio (mass ratio) of water to the plant-derived raw material is preferably in the range of 1:1 to 1:10. By setting the ratio of water to the plant-derived raw material to be within the above-described range, the hydrolysis reaction can be efficiently performed. The water used in the heat treatment step may be water added separately from the plant-derived raw material; or a portion of the water may be water originally contained in the plant-derived raw material.

In the heat treatment step, other chemicals may also be added, in addition to the plant-derived raw material and water. Examples of such other chemicals include alkalis, acids, and chelating agents. Further, chemicals that directly or indirectly assist the depolymerization of polysaccharides, such as a scale inhibitor, a pitch control agent, and an ionic liquid, may also be added.

The heat treatment step is a step of heating a plant-derived raw material in the presence of water. The heating temperature (liquid temperature) in this step is preferably 30° C. or higher, more preferably 50° C. or higher, even more preferably 75° C. or higher, still even more preferably 90° C. or higher, particularly preferably 100° C. or higher, and most preferably 120° C. or higher. On the other hand, the heating temperature (liquid temperature) is preferably 300° C. or lower, more preferably 250° C. or lower, and even more preferably 200° C. or lower.

The treatment time in the heat treatment step can be determined, as appropriate, according to the treatment temperature. The treatment time is, for example, preferably 5 minutes or more, more preferably 10 minutes or more, and even more preferably 20 minutes or more. The P factor expressed by the following formula is a product of the heat treatment temperature and the heat treatment time. It is preferable to adjust the P factor within a preferred range.

$$P = \int_{t_0}^{t} \frac{k_{H1(T)}}{k_{100°\,C.}} \cdot dt = \int_{t_0}^{t} \mathrm{Exp} \cdot \left(40.48 - \frac{15106}{T}\right) \cdot dt$$

In the above formula, P represents a P factor, T represents an absolute temperature (° C.+273.5), t represents the heat treatment time, and $K_{H1(T)}/K_{100°\,C.}$ represents the relative rates of hydrolysis of glycoside bonds.

In the heat treatment step, the P factor is preferably set at 200 or more, more preferably 250 or more, and even more preferably 300 or more. On the other hand, the P factor is preferably 1000 or less. In the heat treatment step, the P factor is adjusted as appropriate so that the average degree of polymerization of xylooligosaccharide is within a desired range, and the molecular weight of the obtained pentosan polysulfate can be thereby adjusted.

In the heat treatment step, the pH value of the solution containing a plant-derived raw material is preferably pH 9 or less, more preferably pH 8 or less, and even more preferably pH 7 or less. That is, the heat treatment step is preferably performed under non-alkaline conditions. The pH value described above refers to the pH of the solution before the heat treatment.

In the heat treatment step, a raw material-derived acid may be dissociated, and acid hydrolysis may be at least partially carried out. Examples of plant raw material-derived acids include organic acids, such as acetic acid and formic acid. In this case, the pH of the solution containing a plant-derived raw material is further decreased after the acid hydrolysis.

The process for producing pentosan polysulfate preferably comprises a heat treatment step as the first step. This can enhance the efficiency of producing xylooligosaccharide, and further enhance the efficiency of producing pentosan polysulfate. By including the heat treatment step as the first step, the production process can significantly reduce the number of steps required to produce xylooligosaccharide, as compared with the conventional methods. By including a heat treatment under non-alkaline conditions as the first step, the production process can efficiently produce xylooligosaccharide with suppressed coloration because xylooligosaccharide is not substituted with hexenuronic acid.

The depolymerization step is preferably a heat treatment step, but may be a step other than the heat treatment step. For example, when the depolymerization step is an enzyme treatment step, the depolymerization step comprises a step of mixing a plant-derived raw material with an enzyme. Examples of usable enzymes include hemicellulase and the like. Specific examples include commercially available enzyme preparations, such as Cellulosin HC100 (trade name, manufactured by HBI Enzymes Inc.), Cellulosin TP25 (trade name, manufactured by HBI Enzymes Inc.), Cellulosin HC (trade name, manufactured by HBI Enzymes Inc.), Cartazyme (trade name, manufactured by Clariant AG), Ecopulp (trade name, manufactured by Rohm Enzyme GmbH), Sumizyme (trade name, manufactured by Shin Nihon Chemicals Corporation), Pulpzyme (manufactured by Novo Nordisk), and Multifect 720 (Genencor); and xylanase produced by microorganisms belonging to genus *Trichoderma*, genus *Thermomyces*, genus *Aureobasidium*, genus *Streptomyces*, genus *Aspergillus*, genus *Clostridium*, genus *Bacillus*, genus *Thermotoga*, genus *Thermoascus*, genus *Cardoceram*, genus *Thermomonospora*, or the like.

In the enzymatic treatment step, an enzyme is added to a solution prepared by mixing a plant-derived raw material with water. The temperature of the solution during this treatment is preferably 10° C. or higher and 90° C. or lower, and more preferably 30° C. or higher and 60° C. or lower. The temperature of the solution is preferably a temperature close to the optimal temperature of the enzyme used. The pH of the solution is also preferably adjusted to a range in which the activity of the enzyme is enhanced. For example, the pH of the solution is preferably adjusted to a pH of 3 or more and a pH of 10 or less.

When the depolymerization step is an alkali treatment step or an acid treatment step, the depolymerization step comprises a step of mixing a plant-derived raw material with an alkaline solution or an acid solution. In the alkali treatment step, sodium hydroxide or potassium hydroxide is preferably added. In the acid treatment step, hydrochloric acid, sulfuric acid, acetic acid, or the like is preferably added. In above cases also, heating or pressurization may be carried out, as appropriate.

When the depolymerization step is at least one selected from an enzyme treatment step, an alkali treatment step, and an acid treatment step, the production method may further comprise, after the treatment step, a squeezing step, an extraction step, a heating step, a filtration step, a separation step, a purification step, a concentration step, a desalination step, or the like. The method may further comprise a molecular weight reducing step after the treatment step. Examples of other steps include the steps described in JP2003-183303A, the contents of which are incorporated herein by reference.

Filtration Step

In the method for producing pentosan polysulfate, the first step may further comprise a filtration step after the depolymerization step described above. In the filtration step, the reaction mixture is separated into solids of the plant-derived raw material, and a solution other than the solids. More specifically, by including a filtration step after the depolymerization step, the reaction product is separated into a filtrate and solids, which are used as a pulp raw material. The solids used as a pulp raw material are subjected to a digestion step or the like as a post-step to provide a cellulose raw material (dissolving pulp).

The recovered filtrate can be divided into a gas layer and a liquid layer. Since the gas layer contains a large amount of furfurals, these furfurals can be recovered and isolated. On the other hand, the liquid layer contains a large amount of hemicellulose comprising acidic xylooligosaccharide and neutral xylooligosaccharide. In the step described below, acidic xylooligosaccharide or neutral xylooligosaccharide contained in this liquid layer can be separated and purified.

Separation/Purification Step

In the method for producing pentosan polysulfate, the first step may further comprise a separation/purification step after the depolymerization step. When the first step comprises the filtration step described above, a separation/purification step is preferably provided after the filtration step.

The first step may comprise a separation/purification step immediately after the depolymerization step. However, the first step preferably comprises a filtration step after the depolymerization step; and a step of separating the desired xylooligosaccharide from the obtained filtrate, and purifying the xylooligosaccharide. The filtration step may be provided as a part of the separation/purification step, or may be provided as one step that is independent from the separation/purification step. The separation/purification step is a step of separating and purifying acidic xylooligosaccharide or neutral xylooligosaccharide. Since the filtrate obtained in the filtration step contains acidic xylooligosaccharide and neutral xylooligosaccharide, the separation/purification step is also a step of sorting acidic xylooligosaccharide or neutral xylooligosaccharide.

In the separation/purification step, for example, ion exchange chromatography, affinity chromatography, gel filtration, ion exchange treatment, NF membrane treatment, UF membrane treatment, RO membrane treatment, activated carbon treatment, or like methods are preferably used. In the separation/purification step, it is also preferable to perform the above methods in combination. Among these, ion exchange chromatography can be performed in the separation/purification step to thereby selectively separate and purify acidic xylooligosaccharide or neutral xylooligosaccharide. For example, in ion exchange chromatography, acidic xylooligosaccharide is adsorbed to thereby obtain neutral xylooligosaccharide from the unadsorbed fraction. Specifically, sugar liquid is first treated with a strong cation exchange resin to remove metal ions from the sugar liquid. Subsequently, using a strong anion exchange resin, sulfate ions or the like are removed from the sugar liquid. The resulting sugar liquid is treated with a weak anion exchange resin to adsorb acidic xylooligosaccharide on the resin. Neutral xylooligosaccharide is obtained from the unadsorbed fraction. On the other hand, the acidic oligosaccharide adsorbed on the resin is eluted with a low-concentration salt (NaCl, CaCl$_2$, KCl, MgCl$_2$, etc.) to thereby obtain an acidic xylooligosaccharide solution containing small quantities of impurities.

Concentration Step

In the method for producing pentosan polysulfate, the first step may further comprise a concentration step. The concentration step is preferably provided, for example, after the filtration step and before the separation/purification step. By including such a concentration step, the separation/purification step can be more efficiently performed, and the efficiency of producing pentosan polysulfate can be enhanced.

Examples of the concentration step include a membrane treatment step using an NF membrane, an ultrafiltration membrane, a reverse osmosis membrane, or the like; a concentration step using evaporation or the like; and the like.

In the concentration step, the solution is preferably concentrated, so that the content of the desired xylooligosaccharide is 10% or more and 80% or less, and more preferably 20% or more and 60% or less, based on the total mass of the concentrate.

Dehydration Step

The xylooligosaccharide obtained in the first step may be in the form of a xylooligosaccharide solution. The xylooligosaccharide may also be obtained in the form of a xylooligosaccharide concentrate or a xylooligosaccharide powder by being subjected to a dehydration step. When a xylooligosaccharide powder is to be produced, the production method preferably further comprises a powdering step after the separation/purification step. By including a dehydration step in the present invention, sulfation in the sulfation step described below can be performed more efficiently.

In the powdering step, the xylooligosaccharide solution obtained in the separation/purification step is treated, for example, using a spray dryer, a freeze-drying machine, a hot-air drying machine, or a water-soluble organic solvent, to thereby obtain a xylooligosaccharide powder.

Second Step

Sulfation Step

In the second step, the xylooligosaccharide obtained in the first step is sulfated to obtain pentosan polysulfate. That is, the second step comprises a sulfation step.

In the sulfation step, sulfuric acid or a sulfuric acid derivative is added to the xylooligosaccharide solution to sulfate the xylooligosaccharide. Examples of the sulfuric acid derivative include sulfur trioxide pyridine complex, chlorosulfonic acid, and the like. In this step, the concentration of the xylooligosaccharide solution is preferably 0.1 mass % or more and 20 mass % or less, and sulfuric acid is preferably added to the xylooligosaccharide solution having such a concentration to achieve a concentration of 0.1 mass % or more and 50 mass % or less. The xylooligosaccharide solution after addition of sulfuric acid preferably has a pH of 1 or more and a pH of 9 or less.

Post-Sulfation Purification Step

In the method for producing pentosan polysulfate, the second step may further comprise a post-sulfation purification step after the sulfation. By including such a post-sulfation purification step, a high-purity pentosan polysulfate can be obtained.

In the post-sulfation purification step, centrifugation, membrane filtration, dialysis, water-soluble organic solvent treatment, activated carbon treatment, or like method is preferably used. Among these, water-soluble organic solvent treatment and activated carbon treatment are preferably used, because sulfonated pentosan polysulfate can be selectively separated and purified.

Powdering Step

In the second step, sulfated pentosan polysulfate may be obtained in the form of a pentosan polysulfate solution, or in the form of a pentosan polysulfate powder, which is produced by being subjected to a powdering step. When a pentosan polysulfate powder is to be produced, the production method preferably further comprises a powdering step after the post-sulfation purification step.

As the powdering step, for example, the pentosan polysulfate solution obtained in the post-sulfation purification step can be treated using a spray dryer, a freeze-drying machine, a hot-air drying machine, a water-soluble organic solvent, or the like, to thereby obtain a pentosan polysulfate powder.

Deacetylation Step

In the production of pentosan polysulfate, deacetylation may be performed. The deacetylation step is preferably performed at any stage after the depolymerization step. The deacetylation step can reduce the acetyl group content of pentosan polysulfate. Specifically, the deacetylation step is a step of adding a base to a solution containing a substance obtained from a plant-derived raw material, such as xylooligosaccharide, (also referred to herein as a "solution containing xylooligosaccharide or the like") so as to adjust the solution to pH 11 or more. In the deacetylation step, the solution obtained after the depolymerization, the filtrate obtained by the filtration step, the solution containing xylooligosaccharide after the separation/purification step and before the sulfation step, the solution containing xylooligosaccharide after the sulfation step (pentosan polysulfate), or the like may have a pH of 11 or more. Among these solutions, when the solution containing xylooligosaccharide after the separation/purification step and before the sulfation step is adjusted to pH 11 or more, a pentosan polysulfate having a stable quality and a reduced acetyl group content can be obtained, and the sites where acetyl groups were bound can also be sulfated. Therefore, the sulfation efficiency and the efficiency of producing pentosan polysulfate can be improved. When the solution containing xylooligosaccharide (pentosan polysulfate) obtained after the sulfation step is adjusted to pH 11 or more, the purification step can be performed more efficiently. The solution containing xylooligosaccharide or the like is preferably an aqueous solution. The solution containing xylooligosaccharide may also be referred to herein as the xylooligosaccharide solution.

The pH in the deacetylation step is preferably pH 11 to 14, and more preferably pH 12 to 13. The solution to be subjected to the deacetylation step is preferably maintained at pH 11 or more for 0.5 hours or more, more preferably at pH 11 or more for 1.0 hour or more, even more preferably at pH 11 or more for 2.0 hours or more, and particularly preferably at pH 11 or more for 3.0 hours or more. In particular, when the pH is less than 12, the solution is preferably maintained for 1.0 hour or more. Particularly preferred conditions may be, for example, conditions for maintaining the solution at pH 12 to 13 for 3 hours or more.

While the solution is maintained in the above-described pH range, the solution is preferably stirred. The temperature applied while the solution is maintained in the above-described pH range is not particularly limited, and is preferably room temperature.

In the deacetylation step, a base may be added to a solution to be subjected to the deacetylation step (a solution containing xylooligosaccharide or the like). The base to be added is not particularly limited, as long as the desired pH can be achieved. The base is preferably sodium hydroxide.

The deacetylation step may comprise a pH adjustment step of adjusting, to less than pH 11, the pH of a solution that has pH 11 or more, which results from the addition of a base after being maintained at the above-described pH. In the pH adjustment step, the pH value of the solution may be adjusted to, for example, pH 9 or less, pH 8 or less, pH 7 or less, pH 6 or less, pH 5 or less, pH 4 or less, or the like. The adjustment may be performed by adding an acid. Examples of usable acids include hydrochloric acid.

The deacetylation step preferably comprises a desalination step after the pH adjustment step. The obtained salt can be removed, for example, using a dialysis membrane or an NF membrane.

The deacetylation step may further comprise a step of powdering the obtained product for the subsequent treatment.

Other Steps
Molecular Weight Adjustment Step

Figure 2:
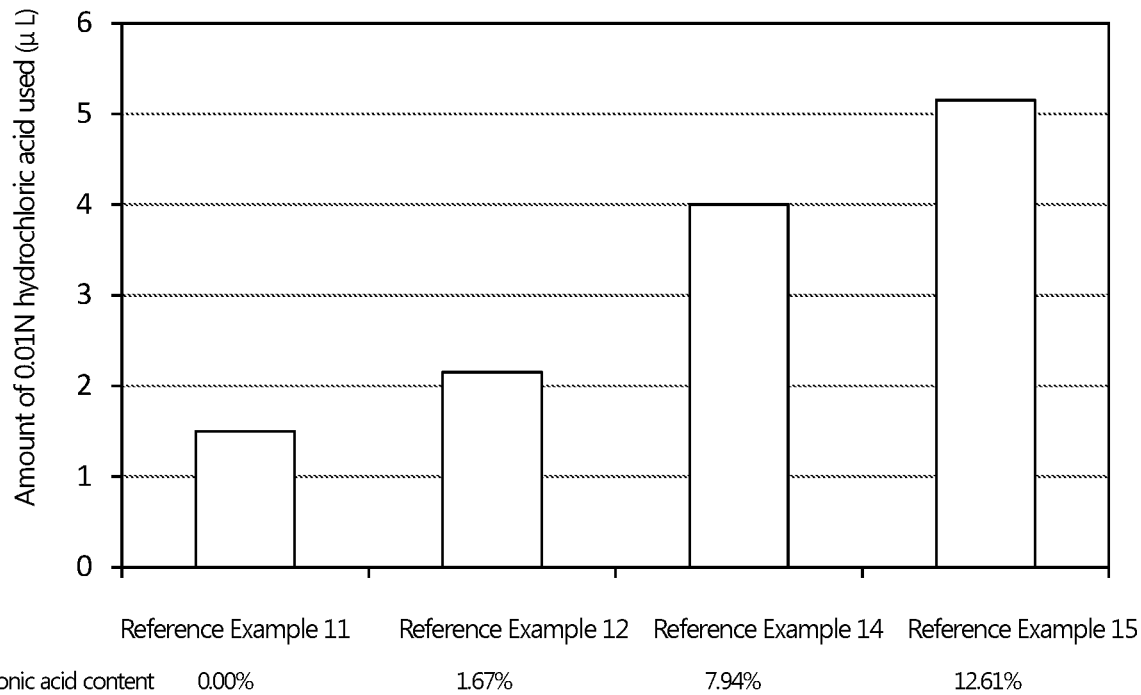
FIG. 2 is a diagram showing the relationship between the uronic acid content of pentosan polysulfate and the amount of a 0.01 N aqueous hydrochloric acid solution required to adjust the pH from pH 6 to pH 4.

The method for producing pentosane polysulfate may further comprise a molecular weight adjustment step between the first step and the second step. FIG. 2 is a flow diagram including a molecular weight adjustment step between the first step and the second step. As shown in FIG. 2, in the molecular weight adjustment step, the molecular weight of the xylooligosaccharide obtained in the first step is adjusted. For example, in the molecular weight adjustment step, the molecular weight of the xylooligosaccharide can be reduced.

In the molecular weight adjustment step, for example, an acid treatment, an alkali treatment, an enzyme treatment, an NF membrane treatment, a UF membrane treatment, an RO membrane treatment, a gel filtration treatment, an activated carbon treatment, an ion exchange treatment, an electrodialysis treatment, or the like can be performed to thereby obtain pentosan polysulfate having a desired weight average molecular weight. Further, in the molecular weight adjustment step, a method comprising performing a membrane treatment or the like to selectively recover pentosan polysulfate having a desired weight average molecular weight can also be used.

Post-Molecular-Weight-Adjustment Separation/Purification Step

The method for producing pentosan polysulfate may further comprise a post-molecular-weight-adjustment separation/purification step, after the molecular weight adjustment step. Examples of the post-molecular-weight-adjustment separation/purification step may include gel filtration, an ion exchange treatment, an NF membrane treatment, a UF membrane treatment, an RO membrane treatment, an electrodialysis treatment, an activated carbon treatment, a water-soluble organic solvent treatment, a chromatographic treatment, and the like. When the production method includes such a post-molecular-weight-adjustment separation/purification step, xylooligosaccharide having a desired molecular weight obtained in the molecular weight adjustment step can be selectively recovered, and pentosan polysulfate having a narrow molecular weight distribution can be efficiently obtained.

EXAMPLES

The features of the present invention are described below more specifically with reference to Production Examples. The materials, amounts used, proportions, treatment content, treatment procedures, and the like described in the following Production Examples can be appropriately changed to the extent that such changes do not depart from the spirit of the present invention. Accordingly, the scope of the present invention should not be construed as being limited by the following specific examples.

Moisturizing Performance of Pentosan Polysulfate

Example 1

Production of Acidic Xylooligosaccharide 40 parts by mass of water was added to 10 parts of wood chips (hardwood), and heat treatment was performed at 160° C. for 3 hours. The resulting mixture was then subjected to solid-liquid separation with a Screw Press (manufactured by Shinryo Seisakusho: 250×1000 SPH-EN), and the filtrate was recovered. The filtrate was filtered through a bag filter with a micron rate of 1 μm (manufactured by ISP Filters). After 5 parts by mass of activated carbon (PM-SX; manufactured by Mikura Kasei Kabushiki Kaisha) was added to the obtained filtrate and treatment was allowed to proceed at 50° C. for 2 hours, the reaction mixture, including the activated carbon, was further filtered through a ceramic filter with a micron rate of 0.2 μm (manufactured by Nihon Pall Co., Ltd.) to recover a clear filtrate. After the clear filtrate was concentrated 20 times with a reverse osmosis membrane (NTR-7450; manufactured by Nitto Denko Corporation) to obtain a concentrated sugar liquid, the concentrated sugar liquid was passed at SV 1.5 through a 4-bed 4-tower type ion exchange resin system consisting of a strong cationic resin (PK-218; manufactured by Mitsubishi Chemical Corporation), a weak anionic resin (WA30; manufactured by Mitsubishi Chemical Corporation), a strong cationic resin (PK-218; manufactured by Mitsubishi Chemical Corporation), and a weak anionic resin (WA30; manufactured by Mitsubishi Chemical Corporation). Acidic xylooligosaccharide was adsorbed on the weak anionic resin of the second and fourth towers. A 50 mM sodium chloride aqueous solution was then passed through the second and fourth towers at SV 1.5 to recover an acidic xylooligosaccharide solution with an average polymerization degree of less than 8. Thereafter, the obtained acidic xylooligosaccharide solution was powdered using a spray dryer (manufactured by Okawara Kogyo Co., Ltd.).

Production of Pentosan Polysulfate Sodium 25 mL of N,N-dimethylformamide, 10 g of sulfur trioxide pyridine complex, and 2 g of acidic xylooligosaccharide powder produced by the method described above were placed in a 100-mL separable flask, and a reaction was allowed to proceed at 40° C. for 3 hours. After cooling, the obtained reaction mixture was added dropwise to 200 mL of ethanol. The generated precipitate was collected by filtration, and 10 mL of water was added to dissolve the precipitate therein. A sodium hydroxide solution was added to the obtained solution to adjust the solution to pH 10. The resulting solution was added dropwise to 200 mL of ethanol, and the obtained precipitate was collected by filtration. Thereafter, 10 mL of water was added to dissolve the precipitate therein, and activated carbon was added to the solution. The resulting mixture was stirred and then filtered. The procedure of adding the obtained filtrate dropwise to 200 mL of ethanol and then collecting the precipitate by filtration was repeated three times for purification. Pentosan polysulfate sodium was thus obtained. Distilled water was added to the obtained pentosan polysulfate sodium to prepare a topical preparation containing pentosan polysulfate sodium in a concentration of 1 mass %.

Example 2

50 parts by mass of 3N Sodium hydroxide was added to 10 parts of wood chips (hardwood), and heat treatment was performed at 155° C. for 2 hours. After cooling, the resulting mixture was subjected to solid-liquid separation with a Screw Press (250×1000 SPH-EN; manufactured by Shinryo Seisakusho). The obtained solid residue was washed with ion exchange water three times. 100 parts by mass of 1N sodium hydroxide was added to 10 parts by mass of the obtained solid residue, and heat treatment was performed at 70° C. for 3 hours. The resulting mixture was then subjected to solid-liquid separation with a Screw Press (250×1000 SPH-EN; manufactured by Shinryo Seisakusho), and the filtrate was recovered. The filtrate was neutralized by adding 1N hydrochloric acid, and the resulting precipitate was collected by filtration. The obtained precipitate was fully washed with ion exchange water, and then dried under reduced pressure to prepare an acidic xylooligosaccharide. Except for the above-described procedure, pentosan polysulfate sodium was obtained in the same manner as in Example 1. Distilled water was added to the obtained pentosan polysulfate sodium to prepare a topical preparation containing pentosan polysulfate sodium in a concentration of 1 mass %.

Comparative Example 1

In Comparative Example 1, distilled water was used as a topical preparation.

Analysis and Evaluation

Weight Average Molecular Weight of Pentosan Polysulfate Sodium

The pentosan polysulfate sodium obtained in each of the Examples was passed through a GPC column (TSKgel G2000SWXL; manufactured by Tosoh Corporation) using 300 mM sodium chloride/50 mM sodium acetate buffer (pH 4.0) as an eluent to perform the molecular weight distribution measurement. The weight average molecular weight and the molecular weight distribution (dispersion degree) of pentosan polysulfate sodium obtained in each of the Examples were measured using pullulan (weight average molecular weight: 1,080-47,100; manufactured by Sigma-Aldrich) as a calibration curve sample.

Sulfur Content

The sulfur content of pentosan polysulfate sodium was measured by the oxygen flask combustion method described in the Japanese Pharmacopoeia.

Uronic Acid Content

The pentosan polysulfate sodium obtained in each of the Examples was dissolved in water to a concentration of 0.5 mg/mL. 1 mL of this solution was placed in a test tube. While the solution was cooled in ice water, 5 mL of borax/sulfuric acid solution was added, and the mixture was heated in a water bath for 10 minutes. The resulting mixture was then cooled with ice water, 0.2 mL of a carbazole reagent was added, and the mixture was heated in a water bath for 15 minutes. 1 mL each of standard solutions containing D-glucuronic acid in concentrations of 10 mL/mL, 20 µg/mL, 30 µg/mL, 40 µg/mL, and 50 µg/mL were individually placed in other test tubes; and the same procedure as above was performed. Further, 1 mL of water was also subjected to the same procedure, and the resulting liquid was used as a control. The absorbance at a wavelength of 530 nm was measured. A calibration curve was prepared from the absorbance of the standard solutions. The uronic acid content of pentosan polysulfate sodium was measured using the calibration curve.

TABLE 1

| | Example 1 | Example 2 |
|---|---|---|
| Weight average molecular weight (Mw) | 3705 | 25487 |
| Dispersion degree | 1.16 | 1.31 |
| Sulfur content (mass %) | 18.8 | 15.3 |
| Uronic acid content (mass %) | 6.97 | 6.38 |

Water Content of the Stratum Corneum

After forearm portions of subjects were thoroughly washed with soap, and water was removed, acclimation was performed in an environment of 20 to 25° C. for 5 minutes. Three 2×2 cm regions were set inside the forearm portion of each subject, and water content of the stratum corneum (µS (microsiemens)) of each region was measured using a SKICON-200EX (manufactured by IBS Co., Ltd.) (water content of the stratum corneum A). Thereafter, 20 µL of the topical preparations obtained in the Examples and Comparative Example were uniformly applied to each of the 2×2 cm regions set inside the forearm. The water content of the stratum corneum (µS) 3 minutes after the application was measured (water content of the stratum corneum B).

TABLE 2

| | Example 1 | Example 2 | Comparative Example 1 |
|---|---|---|---|
| Water content of the stratum corneum A (µS) | 30 | 33 | 37 |
| Water content of the stratum corneum B (µS) | 289 | 219 | 46 |

As shown in Table 2, as compared with the results obtained using distilled water in the Comparative Example, the topical preparations obtained in the Examples achieved a high water content of the stratum corneum even 3 minutes after the application. The results thus show that the topical preparations obtained in the Examples have moisturizing properties.

Pentosan Polysulfates Having Different Uronic Acid Contents

Production of Acidic Xylooligosaccharide 50 parts by mass of water was added to 10 parts of wood chips (hardwood), and heat treatment was performed at 165° C. for 3 hours. The resulting mixture was then subjected to solid-liquid separation with a Screw Press (250×1000 SPH-EN; manufactured by Shinryo Seisakusho), and the filtrate was recovered. The filtrate was filtered through a bag filter with a micron rate of 1 μm (manufactured by ISP Filters). After 5 parts by mass of activated carbon (PM-SX; manufactured by Mikura Kasei Kabushiki Kaisha) was added to the obtained filtrate and treatment was allowed to proceed at 50° C. for 2 hours, the reaction mixture, including the activated carbon, was further filtered through a ceramic filter with a micron rate of 0.2 μm (manufactured by Nihon Pall Co., Ltd.) to recover a clear filtrate. After the clear filtrate was concentrated 20 times with a reverse osmosis membrane (NTR-7450; manufactured by Nitto Denko Corporation) to obtain a concentrated sugar liquid, the concentrated sugar liquid was passed at SV 1.5 through a 4-bed 4-tower type ion exchange resin system consisting of a strong cationic resin (PK-218; manufactured by Mitsubishi Chemical Corporation), a weak anionic resin (WA30; manufactured by Mitsubishi Chemical Corporation), a strong cationic resin (PK-218; manufactured by Mitsubishi Chemical Corporation), and a weak anionic resin (WA30; manufactured by Mitsubishi Chemical Corporation). Acidic xylooligosaccharide was adsorbed on the weak anionic resin of the second and fourth towers. A 50 mM sodium chloride aqueous solution was then passed through the second and fourth towers at SV 1.5 to thereby recover an acidic xylooligosaccharide solution. Sodium hydroxide was added to the obtained acidic xylooligosaccharide solution to achieve a pH of 13, and the resulting mixture was stirred at room temperature for 3 hours for deacetylation. After hydrochloric acid was added to the resulting solution to achieve a pH of less than 5 and the obtained salt was removed using a dialysis membrane (Spectra/Por 7, CE membrane, MWCO 100-500; manufactured by Spectrum), the resulting mixture was powdered using a freeze-drying machine (manufactured by Eyela).

Production of Neutral Xylooligosaccharide 50 parts of water was added to 10 parts by mass of wood chips (hardwood), and heat treatment was performed at 165° C. for 3 hours. The resulting mixture was then subjected to solid-liquid separation using a Screw Press (250×1000 SPH-EN; manufactured by Shinryo Seisakusho), and the filtrate was recovered. The filtrate was filtered through a bag filter with a micron rate of 1 μm (manufactured by ISP Filters). After 5 parts by mass of activated carbon (PM-SX; manufactured by Mikura Kasei Kabushiki Kaisha) was added to the obtained filtrate and treatment was allowed to proceed at 50° C. for 2 hours, the reaction mixture, including the activated carbon, was further filtered through a ceramic filter with a micron rate of 0.2 μm (manufactured by Nihon Pall Co., Ltd.) to recover a clear filtrate. After the clear filtrate was concentrated 20 times with a reverse osmosis membrane (NTR-7450; manufactured by Nitto Denko Corporation) to obtain a concentrated sugar liquid, the concentrated sugar liquid was passed at SV 1.5 through a 4-bed 4-tower type ion exchange resin system consisting of a strong cationic resin (PK-218; manufactured by Mitsubishi Chemical Corporation), a weak anionic resin (WA30; manufactured by Mitsubishi Chemical Corporation), a strong cationic resin (PK-218; manufactured by Mitsubishi Chemical Corporation), and a weak anionic resin (WA30; manufactured by Mitsubishi Chemical Corporation) to thereby recover a neutral xylooligosaccharide solution. Sodium hydroxide was added to the obtained neutral xylooligosaccharide solution to achieve a pH of 13, and the resulting mixture was stirred at room temperature for 3 hours for deacetylation. After hydrochloric acid was added to the resulting solution to achieve a pH of less than 5 and the obtained salt was removed using a dialysis membrane (Spectra/Por 7, CE membrane, MWCO 100-500; manufactured by Spectrum), the resulting mixture was powdered using a freeze-drying machine (manufactured by Eyela).

Production of Pentosan Polysulfate Sodium

Reference Example 11

25 mL of N,N-dimethylformamide, 12.4 g of sulfur trioxide pyridine complex, and 1.5 g of neutral xylooligosaccharide powder produced by the method described above were placed in a 100-mL separable flask, and a reaction was allowed to proceed at 40° C. for 3 hours. After cooling, the obtained reaction mixture was added dropwise to 500 mL of ethanol. The generated precipitate was collected by filtration, and 30 mL of water was added to dissolve the precipitate therein. A sodium hydroxide solution was added to the obtained solution to achieve a pH of 10. The resulting solution was added dropwise to 500 mL of ethanol, and the obtained precipitate was then collected by filtration. Thereafter, 30 mL of water was added to dissolve the precipitate therein, and activated carbon was added to the solution and stirred, followed by filtration. The filtrate was concentrated using an evaporator, and powdered using a freeze-drying machine (manufactured by Eyela).

Reference Example 12

Pentosan polysulfate sodium was obtained in the same manner as in Reference Example 11, except that a mixture of 1.125 g of neutral xylooligosaccharide powder and 0.375 g of acidic xylooligosaccharide produced by the above method comprising the deacetylation step was used in place of 1.5 g of the neutral xylooligosaccharide powder of Reference Example 11.

Reference Example 13

Pentosan polysulfate sodium was obtained in the same manner as in Reference Example 11, except that a mixture of 0.75 g of neutral xylooligosaccharide powder and 0.75 g of acidic xylooligosaccharide produced by the above method comprising the deacetylation step was used in place of 1.5 g of the neutral xylooligosaccharide powder of Reference Example 11.

Reference Example 14

Pentosan polysulfate sodium was obtained in the same manner as in Reference Example 11, except that a mixture of 0.375 g of neutral xylooligosaccharide powder and 1.125 g of acidic xylooligosaccharide produced by the above method comprising the deacetylation step was used in place of 1.5 g of the neutral xylooligosaccharide powder of Reference Example 11.

Reference Example 15

Pentosan polysulfate sodium was obtained in the same manner as in Reference Example 11, except that 1.5 g of acidic xylooligosaccharide produced by the above method comprising the deacetylation step was used in place of 1.5 g of the neutral xylooligosaccharide powder of Reference Example 11.

Physical Property Values

The uronic acid content, sulfur content, average molecular weight, and acetyl content of the pentosan polysulfates obtained in Reference Examples 11 to 15 were measured in the following manner. Table 3 shows the results.

Uronic Acid Content

About 10 mg of pentosan polysulfate sodium obtained in each of Reference Examples 11 to 14 was weighed out and dissolved in distilled water to make the volume exactly 25 mL. 1 mL of each solution was placed in a test tube. While the solution was cooled in ice water, 5 mL of a 0.025M sodium tetraborate/sulfuric acid solution was added and mixed, and the resulting mixture was heated in a water bath for 10 minutes. Immediately after heating, the resulting mixture was ice-cooled, and 0.2 mL of a carbazole reagent was added and mixed. The resulting mixture was heated in a water bath for 15 minutes, and then allowed to cool to obtain a sample solution. Separately, glucuronic acid standard stock solutions in a concentration of 10 to 100 µg/mL were prepared and subjected to the same procedure as above to obtain standard solutions. 1 mL of distilled water was also subjected to the same procedure, and the resulting liquid was used as a control. Absorbance at a wavelength of 530 nm was measured. A calibration curve was prepared from the absorbance of the standard solutions, and the amount of glucuronic acid (g) was determined. The uronic acid content (mass %) was calculated according to the following formula. When the quantitative value was negative, it was regarded as 0%.

Uronic acid content (mass %)=Amount of glucuronic acid (µg)/(Weighed amount of pentosan polysulfate sodium×1/25)/10

Sulfur Content

The sulfur content was measured by the oxygen flask combustion method described in the Japanese Pharmacopoeia.

Weight Average Molecular Weight

The weight average molecular weight (Mw) of pentosan polysulfate was measured by GPC (gel permeation chromatography). YMC-Pack Diol-300 and YMC-Pack Diol-60 (both manufactured by YMC) connected to each other can be used as a GPC column. GPC was performed under the following conditions.

Eluent: 25 mM potassium dihydrogen phosphate/25 mM dipotassium hydrogen phosphate/50 mM potassium chloride Flow rate: 0.7 mL/min Measurement temperature: 40° C.

Detector: refractive index detector

Acetyl Group Content 35 mg of sodium 3-(trimethylsilyl)propionate-2,2,3,3-d4 (Isotec Corporation) was dissolved in heavy water (Kanto Kagaku). Using a 25-mL measuring flask, the solution was diluted to prepare an internal standard solution. The pentosan polysulfate sodium obtained in each of the Examples was weighed (30 mg) and dissolved in 1 mL of the internal standard solution to prepare a solution for use in NMR. The obtained solution was transferred to an NMR sample tube (Kanto Kagaku), and $^1$H-NMR measurement was performed using FT-NMR (JNM-LA400; JEOL Ltd.). The acetyl content was calculated from the integral ratio of the peak for trimethylsilyl of the internal standard substance and the peak for acetyl group of sodium pentosan polysulfate.

Yield

The yield of pentosan polysulfate sodium powder obtained from xylooligosaccharide powder was determined. Table 3 shows the results.

Properties of Solution 2 mL of a 100 mg/mL aqueous pentosan polysulfate sodium solution was placed in a 5-mL vial, and the properties of the solution were confirmed after 4 weeks of storage at 40° C. Table 3 shows the results.

TABLE 3

| | Reference Example 15 | Reference Example 14 | Reference Example 13 | Reference Example 12 | Reference Example 11 |
|---|---|---|---|---|---|
| Weight average molecular weight | 2781 | 2487 | 2387 | 2168 | 2053 |
| Uronic acid content (mass %) | 12.61 | 7.94 | 5.67 | 1.64 | 0.00 |
| Sulfur content (mass %) | 13.28 | 14.33 | 15.12 | 15.09 | 15.34 |
| Acetyl group content (mass %) | 0.00 | 0.00 | 0.00 | 0.00 | 0.00 |
| Yield (g) | 2.40 | 2.24 | 2.89 | 3.02 | 3.85 |
| Appearance of the solution (initial) | Colorless transparent | Colorless transparent | Colorless transparent | Colorless transparent | Colorless transparent |
| Appearance of the solution (4-week storage at 40° C.) | Slightly yellow transparent | Slightly yellow transparent | Colorless transparent | Colorless transparent | Colorless transparent |

The results of Table 3 clearly show that as the uronic acid content is lower, pentosane polysulfate sodium was obtained in a larger amount (with a higher yield). Further, while the aqueous pentosan polysulfate sodium solutions with a high uronic acid content (Reference Example 14 and Reference Example 15) turned yellow after storage at 40° C. for 4 weeks, no changes were observed in the aqueous pentosan polysulfate sodium solutions with a low uronic acid content (Reference Example 11 to and Reference Example 13).

pH Buffering Action 100 mg of pentosan polysulfate obtained in each of Reference Examples 11, 12, 14, and 15 was dissolved in water to make the total volume exactly 100 mL. This solution was adjusted to pH 10 using a 0.01N sodium hydroxide aqueous solution (Kanto Kagaku) with an automatic titrator (DKK Toa Corporation). Titration was then performed using a 0.01N aqueous hydrochloric acid solution (Kanto Kagaku) with the automatic titrator, and the amount of 0.01N aqueous hydrochloric acid solution required to adjust the pH of the pentosan polysulfate solution from pH 6 to pH 4 was calculated.

FIG. 2 shows the results.

The results of FIG. 2 clearly show that pentosan polysulfate with a high uronic acid content has high buffering action at pH 4 to 6.

The invention claimed is:

1. A method of moisturizing the skin of a human or an animal, comprising applying to the skin of a human or an animal at least one pentosan polysulfate compound selected from the group consisting of pentosan polysulfate; pharmaceutically acceptable salts of pentosan polysulfate; pharmaceutically acceptable solvates of pentosan polysulfate; and pharmaceutically acceptable solvates of pharmaceutically acceptable salts of pentosan polysulfate,
wherein the pentosan polysulfate compound has an acetyl group content of 0% by mass to 0.3% by mass.

2. The method according to claim 1, wherein the pentosan polysulfate compound has a uronic acid content of 0.0% by mass to 15.0% by mass.

3. The method according to claim 2, wherein the pentosan polysulfate compound has a uronic acid content of 7.0% by mass to 15.0% by mass.

4. The method according to claim 2, wherein the pentosan polysulfate compound has a uronic acid content of 0.0% by mass to 6.0% by mass.

5. The method according to claim 1, wherein the pharmaceutically acceptable salt of pentosan polysulfate comprises pentosan polysulfate sodium.

6. A method of moisturizing the skin of a human or an animal, comprising applying to the skin of a human or an animal an aqueous solution containing at least one pentosan polysulfate compound selected from the group consisting of pentosan polysulfate; pharmaceutically acceptable salts of pentosan polysulfate; pharmaceutically acceptable solvates of pentosan polysulfate; and pharmaceutically acceptable solvates of pharmaceutically acceptable salts of pentosan polysulfate, in an amount of 0.05% by mass or more and 40% by mass or less, based on the total mass of the aqueous solution,
wherein the pentosan polysulfate compound has an acetyl group content of 0% by mass to 0.3% by mass.

7. The method according to claim 6, wherein the pentosan polysulfate has a uronic acid content of 0.0% by mass to 15.0% by mass.

8. The method according to claim 7, wherein the pentosan polysulfate compound has a uronic acid content of 7.0% by mass to 15.0% by mass.

9. The method according to claim 7, wherein the pentosan polysulfate compound has a uronic acid content of 0.0% by mass to 6.0% by mass.

10. The method according to claim 6, wherein the pharmaceutically acceptable salt of pentosan polysulfate comprises pentosan polysulfate sodium.

11. The method according to claim 6, wherein the pentosan polysulfate compound has a dispersion degree of 1.00 or more and 1.40 or less.

* * * * *